United States Patent [19]

Hower

[11] Patent Number: 4,534,058

[45] Date of Patent: Aug. 6, 1985

[54] ELECTRONIC STETHOSCOPE WITH AUTOMATIC POWER SHUT-OFF

[75] Inventor: Larry H. Hower, New York, N.Y.

[73] Assignee: The Hart Group, Dallas, Tex.

[21] Appl. No.: 480,062

[22] Filed: Mar. 29, 1983

[51] Int. Cl.³ .............................................. H04R 1/46
[52] U.S. Cl. ...................................... 381/67; 128/715
[58] Field of Search ......................... 381/67, 100, 123; 128/715

[56] References Cited

U.S. PATENT DOCUMENTS

| | | | |
|---|---|---|---|
| 2,419,471 | 4/1947 | Thibos | 381/67 |
| 3,087,016 | 4/1963 | Dahl | 381/67 |
| 3,132,208 | 5/1964 | Dymski et al. | 179/1 |
| 3,160,708 | 12/1964 | Andries et al. | 179/1 |
| 3,182,129 | 11/1962 | Clark | 179/1 |
| 3,233,041 | 2/1966 | Croslin | 381/67 |
| 3,247,324 | 4/1966 | Cefaly et al. | 179/1 |
| 3,525,810 | 8/1970 | Adler | 381/67 |
| 3,539,724 | 11/1970 | Keesee | 179/1 |
| 3,858,005 | 12/1974 | Marshall et al. | 179/1 |
| 3,989,895 | 11/1976 | O'Daniel | 381/67 |
| 4,048,444 | 9/1977 | Giampapa | 381/67 |
| 4,071,694 | 1/1978 | Pfeiffer | 179/1 |
| 4,072,822 | 2/1978 | Yamada | 179/1.5 |
| 4,170,717 | 10/1979 | Walshe | 179/1 |
| 4,254,302 | 3/1981 | Walshe | 179/1 |
| 4,362,164 | 12/1982 | Little et al. | 128/639 |
| 4,438,772 | 3/1984 | Slavin | 381/67 |

Primary Examiner—Gene Z. Rubinson
Assistant Examiner—L. C. Schroeder
Attorney, Agent, or Firm—Hubbard, Thurman, Turner & Tucker

[57] ABSTRACT

In an electronic stethoscope which includes a pickup head, a microphone, a tubular accoustic connection between the pickup head and microphone, an amplifier receiving an input from the microphone, a speaker coupled to the output of the amplifier, a binaural headpiece and tubes acoustically coupling the output of the speaker to the binaural headpiece, there is included a switch by means of which a momentary on operation can be achieved and a timer responsive to the switch to couple power to amplifier circuit, the timer adapted to shut power off after a predetermined period of time. Preferably the amplifier is an integrated circuit operational amplifier with a filter circuit which brings up lower frequencies interposed between the amplifier and speaker.

10 Claims, 2 Drawing Figures

ELECTRONIC STETHOSCOPE WITH AUTOMATIC POWER SHUT-OFF

BACKGROUND OF THE INVENTION

This invention relates to medical instruments in general, and more particularly to an improved electronic stethosope which includes superior noise rejection and automatic power shut-off.

Both electronic and accoustic stethoscopes and combinations of these two are well known in the art. A typical example of an electronic stethoscope is that described in U.S. Pat. 3,247,324. A pickup head is accoustically cooupled, by means of a flexible conduit, to a microphone. Signals picked up by the microphone are amplified and provided to a speaker which is accoustically coupled to a conventional binaural headpiece by means of flexible conduits. The particular stethoscope disclosed also permits a direct accoustical connection.

Two basic problems with electronic stethoscopes have been the fact that they do not adequately bring up the low frequencies when filtering out high frequency noises from an external sources such as fluorescent lights and the like and that they are often inadvertently left on causing the battery to drain down and require early replacement.

It is the object of the present invention to provide an improved electronic stethoscope which does not suffer from these disadvantages.

SUMMARY OF THE INVENTION

In accordance with the present invention, an electronic stethoscope which includes a conventional pickup head, a tube accoustically coupling the output of the pickup head to a microphone, an amplifier circuit, and a speaker coupled to a binaural headpiece by flexible connections is provided, in its amplifier circuit, with a filter which is particularly effective in removing unwanted frequencies picked up externally while at the same time amplifying and bringing up desired low frequencies in the 25 to 150-200Hz range. Alternativly a tuneable bandpass filter of a width of one octave and tuneable from 410Hz to 600Hz may be used. In addition, power is supplied to the amplifier circuit through a transistor switch controlled by a timer so that when the device is not in use, even if the off switch is not operated, the amplifier circuit is switched off and current drain is reduced to a minimum.

DETAILED DESCRIPTION

Figure 1:
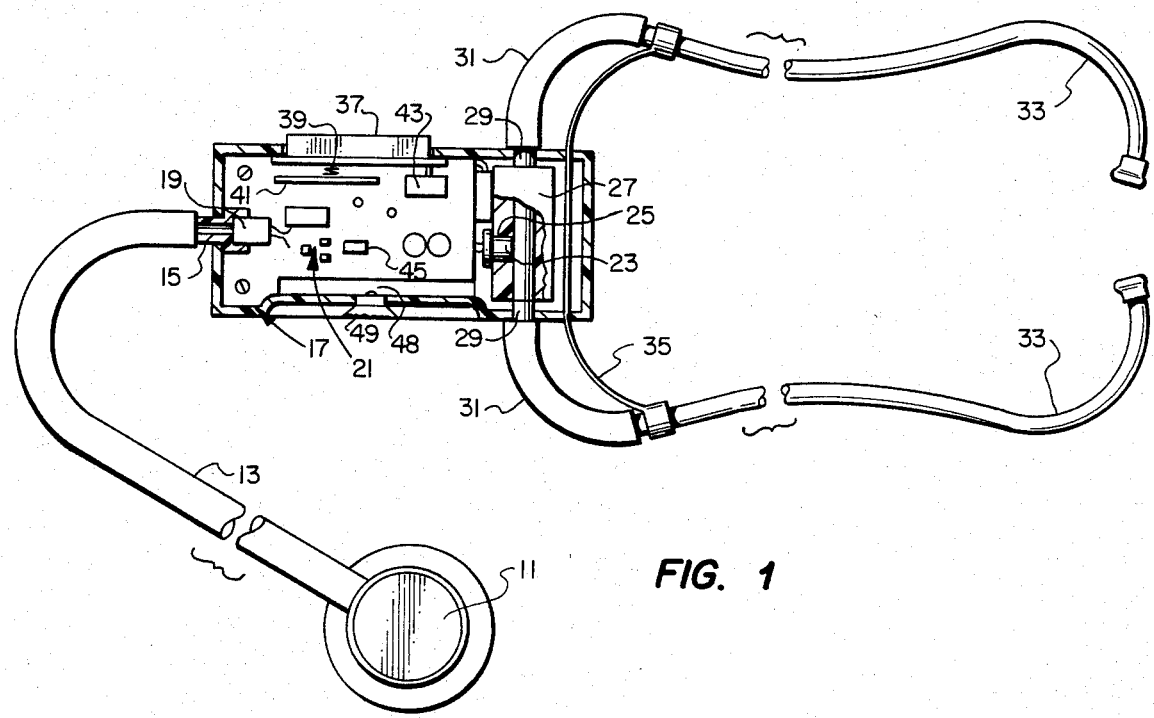
FIG. 1 is a plan view of the stethoscope of the present invention with the cover removed from the central unit, containing the electronic circuits, with portions shown cut-away.

In accordance with the present invention, a conventional stethoscope head 11 is coupled via a flexible tube 13 to an inlet connection 15 on a central unit, generally indicated as 17, containing the electronic circuits for the electronic stethoscope of the present invention. The central unit 17 is essentially a rectangular box having at one end the input coupling 15. The box and couplings can be molded of plastic. At the other end of the coupling 15, a microphone 19 is inserted. Microphone 19 provides an input to an amplifier circuit generally indicated as 21 to be described in more detail below. The output of amplifier circuit 21 is a speaker 23 which is inset into an opening 25 in a coupling block 27. Coupling block 27 has a central bore with tubular extensions 29 on each side to which tubes 31 coupled to the binaural earpieces 33 are connected. Also provided is a support member 35 attached to each of the binaural earpieces, typically made of stainless steel and anchored into the central member 17 with potting or the like. On one side of the central box is a switch bar 37 biased outwardly by a spring 39 acting between the switch bar and a vertical partition 41 in the central box 17. Switch bar 37 acts against a microswitch 43 which is used to trigger a timer contained within a module 45, to provide power for a predetermined period of time. At the end of this time, power is removed from the amplifier circuit.

Figure 2:
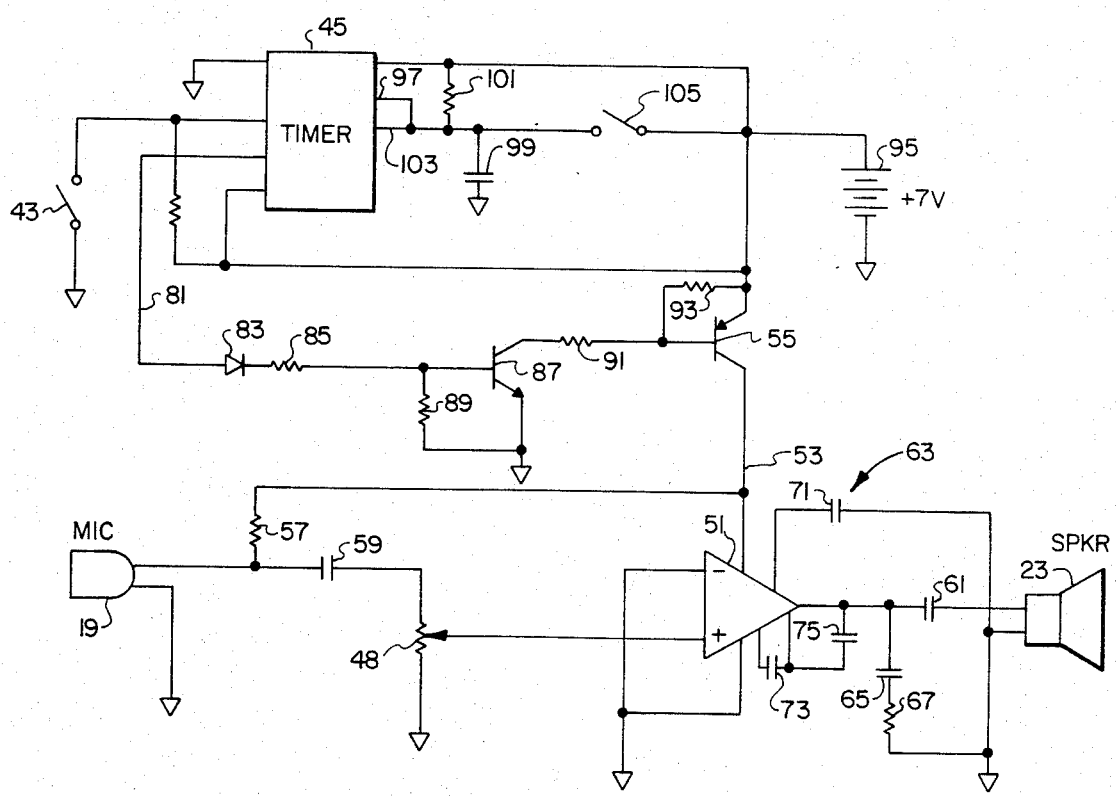
FIG. 2 is a block-circuit diagram of the electronic circuits of FIG. 1.

FIG. 2 is a block-circuit diagram of the eletronic circuits of the stethoscope of the present invention. The upper portion of FIG. 2 comprises the timer for supplying power to the amplifier circuit for a predetermined period of time. The lower part of FIG. 2 illustrates the amplifier circuit with its filter circuits. Power is supplied to the amplifier 51 itself, which is an integrated circuit operational amplifier such as an ALM-386N-1 amplifier via line 53 from a transistor 55 in a manner to be described in more detail below. The other side of the amplifier 51 is grounded in conventional fashion as is its inverting input. Power from line 53 is also provided through a resistor 57, typically -1 K to the microphone 19. The other side of the microphone is coupled to ground. The microphone output is coupled through a coupling capacitor 59 to potentiometer 48. The wiper output of the potentiometer 48 is the input to the noninverting input of amplifier 51. The amplifier output is coupled to the speaker 23 through a coupling capacitor 61. The other side of the speaker is grounded. In addition, associated with the output of the amplifier and with its compensating inputs is a filter circuit generally indicated as 63. This includes a capacitor 65 in series with a resistor 67 between the output of the amplifier and ground. In addition, a capacitor 71 couples the bypass connection to ground with a capacitor 73 coupled between two compensating gain inputs with one side of this capacitor coupled to the output through capacitor 75. Typical values are as follows:

Capacitor 59: 10 UF
Capacitor 61: 1000 UF
Capacitor 65: 0.047 UF
Resistor 67: 10 Ohms.
Capacitor 63: 10 UF
Capacitor 73: 10 UF
Capacitor 75: 0.022 UF
Potentiometer 48: 10K Ohms.

With this circuit and particularly with the chosen values of capacitor 61, capacitor 65 and resistor 67, desired frequencies, i.e., frequencies in the range of 25 to 85-100Hz are enhanced and coupled to the speaker, whereas undesired higher frequencies are filtered out. Alternatively, a bandpass filter with a one octave band and tuneable between 40 and 600Hz may be inserted between amplifier 5L and speaker 23.

In operation, pressing switch 43 triggers a flip-flop in timer 45 causing an output on a line 81, which is coupled through a diode 83 and resistor 85 to the base of a transistor 87. Transistor 87 has its emitter grounded and has a biasing resistor 89 between ground and its base. This signal turns on transistor 87 which is coupled through a resistor 91 to the base of a transistor 55, transistor 55 having a resistor 93 between its emitter and base with its collector coupled to line 53. Transistor 55 is turned on coupling +7 volts from a battery 95 through transistor 55 to line 53 thereby supplying power to the amplifier circuit. At the same time, a transistor switch closure in the timer, which was coupling line 97 to ground, is now opened and a capacitor 99, for example, 10UF, charges through a resistor 101, for example 15 Megohms to give an RC time constant of about 2.5 min. The voltage on the capacitor is coupled into the timer on line 103. This is an input to a comparator in the timer and, when a threshold voltage is reached, the comparator provides an output which resets the flip-flop in the timer removing the signal on line 81, thus, turning off transistors 87 and 55.

Also shown is a switch 105 by means of which the circuit can be shut off when finished using it without waiting for the timer to time out. Closing switch 105 causes the full 7 volts of the supply voltage to be placed on line 103 to immediately cause a reset of the flip-flop in the timer and removal of power.

What is claimed is:

1. In an electronic stethoscope comprising a pickup head; a microphone; a tubular accoustic connection between the pickup head and microphone; an amplifier circuit receiving an input from the microphone; a speaker coupled to the output of the amplifier circuit; a binaural headpiece; and tubular accoustic coupling means coupling the output of the speaker to the binaural headpiece, the improvement comprising: a switch by means of which a momentary on operation can be achieved; and a timer responsive to said switch to couple power to said amplifier circuit, said timer adapted to shut off power after a predetermined period of time.

2. The improvement according to claim 1, wherein said timer comprises:
   (a) an integrated circuit timer;
   (b) an external RC circuit coupled to said timer to establish a timing period; and
   (c) a semiconductor switch coupled to be controlled by the output of said integrated circuit timer for coupling power to said amplifier circuit.

3. The improvement according to claim 1, and further including an additional switch coupled to said timer so as to shut off said timer when said switch is momentarily operated.

4. The improvement according to claim 1, wherein said amplifying circuit comprises an integrated circuit operational amplifier and further including a filter circuit between the output of said integrated circuit amplifier and said speaker.

5. The improvement according to claim 4, wherein said filter contains components selected to enhance lower frequencies in the range of 25 to 85-100Hz by filtering out higher frequencies.

6. The improvement according to claim 4, wherein said filter circuit comprises a capacitor in series with said speaker and the output of said amplifier and a capacitor and resistance in series between the output of said amplifier and ground.

7. An electronic stethoscope comprising a pickup head; a microphone; a tubular accoustic connection between the pickup head and microphone; an amplifier receiving an input from the microphone; a speaker coupled to the output of the amplifier circuit; a binaural headpiece; and tubular accoustic coupling means coupling the output of the speaker to the binaural headpiece, said amplifier comprising an integrated circuit operational amplifier; and including a filter for enhancing lower frequencies by filtering out higher frequencies interposed between the output of said amplifier and said speaker.

8. The improvement according to claim 7, wherein said filter circuit comprises a capacitor in series with said speaker and the output of said amplifier and a capacitor and resistance in series between the output of said amplifier and ground.

9. The improvement according to claim 7, wherein said filter contains components selected to bring up lower frequencies in the range of 25 to 85-100Hz.

10. The improvement according to claim 7 wherein said filter is a tuneable bandpass filter of width one octave, tuneable between center frequencies of about 40 and 600Hz.

* * * * *